United States Patent
Park et al.

(10) Patent No.: US 11,008,332 B2
(45) Date of Patent: May 18, 2021

(54) PHARMACEUTICAL COMPOSITION FOR PREVENTING OR TREATING AGING-RELATED DISEASES CONTAINING DECURSIN DERIVATIVE AS ACTIVE INGREDIENT

(71) Applicant: PRG S&TECH INC., Busan (KR)

(72) Inventors: Bum Joon Park, Busan (KR); Gyu Yong Song, Daejeon (KR); Yu Seok O, Daejeon (KR); Jee Hyun Lee, Daejeon (KR); Eun Ju Yun, Daejeon (KR)

(73) Assignee: PRG S&TECH INC, Busan (KR)

( * ) Notice: Subject to any disclaimer, the term of this patent is extended or adjusted under 35 U.S.C. 154(b) by 71 days.

(21) Appl. No.: 16/605,802

(22) PCT Filed: Apr. 25, 2018

(86) PCT No.: PCT/KR2018/004812
§ 371 (c)(1),
(2) Date: Oct. 17, 2019

(87) PCT Pub. No.: WO2018/199633
PCT Pub. Date: Nov. 1, 2018

(65) Prior Publication Data
US 2020/0048274 A1 Feb. 13, 2020

(30) Foreign Application Priority Data

Apr. 25, 2017 (KR) .................. 10-2017-0052787
Apr. 19, 2018 (KR) .................. 10-2018-0045593

(51) Int. Cl.
*A61P 43/00* (2006.01)
*A61P 17/00* (2006.01)
*C07D 493/04* (2006.01)
*A61K 45/06* (2006.01)

(52) U.S. Cl.
CPC ............ *C07D 493/04* (2013.01); *A61P 17/00* (2018.01); *A61K 45/06* (2013.01)

(58) Field of Classification Search
CPC ........ C07D 493/04; A61P 17/00; A61K 45/06
See application file for complete search history.

(56) References Cited

U.S. PATENT DOCUMENTS

| 9,249,153 B2 * | 2/2016 | Park ................. A61P 35/00 |
| 2010/0167997 A1 | 7/2010 | Kim |
| 2014/0039010 A1 | 2/2014 | Park et al. |

FOREIGN PATENT DOCUMENTS

| EP | 2687216 A2 | 1/2014 |
| JP | 2008-001602 A | 1/2008 |
| JP | 2008-528577 A | 7/2008 |
| JP | 2017/057159 A | 3/2017 |
| JP | 2017-071632 A | 4/2017 |
| KR | 10-2007-0100329 A | 10/2007 |
| KR | 10-2008-0040094 A | 5/2008 |
| KR | 10-2010-0008808 A | 1/2010 |
| KR | 10-2013-0104991 A | 9/2013 |
| KR | 10-1407044 B1 | 7/2014 |
| KR | 10-1674145 B1 | 11/2016 |

OTHER PUBLICATIONS

Harhouri et al Nucleus, 2018, vol. 9, No. 1, 265-276. (Year: 2018).*
Kang et al, Communications Biology, (2021) 4:5, 1-11. (Year: 2021).*
Lee et al European Journal of Medicinal Chemistry 45 (2010) 5567-5575. (Year: 2010).*
International Search Report for PCT/KR2018/004812 dated Aug. 24, 2018 from Korean Intellectual Property Office.
Lee, K. et al., "3D-QSAR Study of Melanin Inhibiting (S)-(+)-Decursin and its Analogues by Pharmacophore Mapping", Bull. Korean Chem. soc., 2012, vol. 33, No. 1, pp. 149-152.
Lee, K. et al., "Synthesis of (S)-(þ)-decursin and its analogues as potent inhibitors of melanin formation in B16 murine melanoma cells", European Journal of Medicinal Chemistry, Dec. 31, 2010., vol. 45, No. 12, pp. 5567-5575.

* cited by examiner

*Primary Examiner* — John Mabry
(74) *Attorney, Agent, or Firm* — Revolution IP, PLLC

(57) ABSTRACT

A composition for preventing or treating an aging-related disease includes a novel decursin derivative as an active ingredient, wherein the novel decursin derivative has exhibited an excellent effect of inhibiting progerin expression and excellent effect of inhibiting binding between progerin and lamin A, and it has been confirmed that the novel decursin derivative prolongs the survival period of animal models in which progerin was induced.

4 Claims, 5 Drawing Sheets

[FIG. 1]
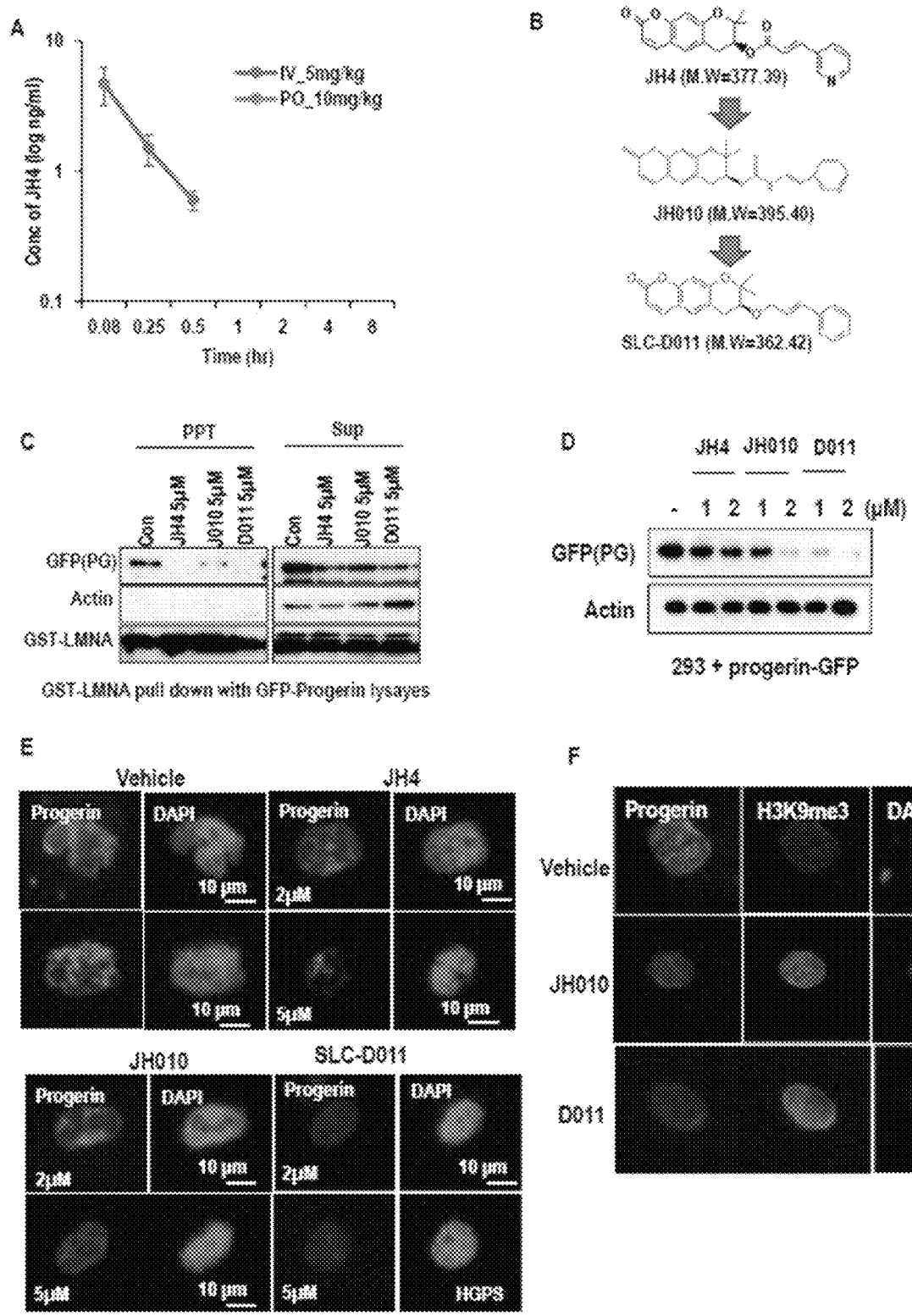

[FIG. 2]
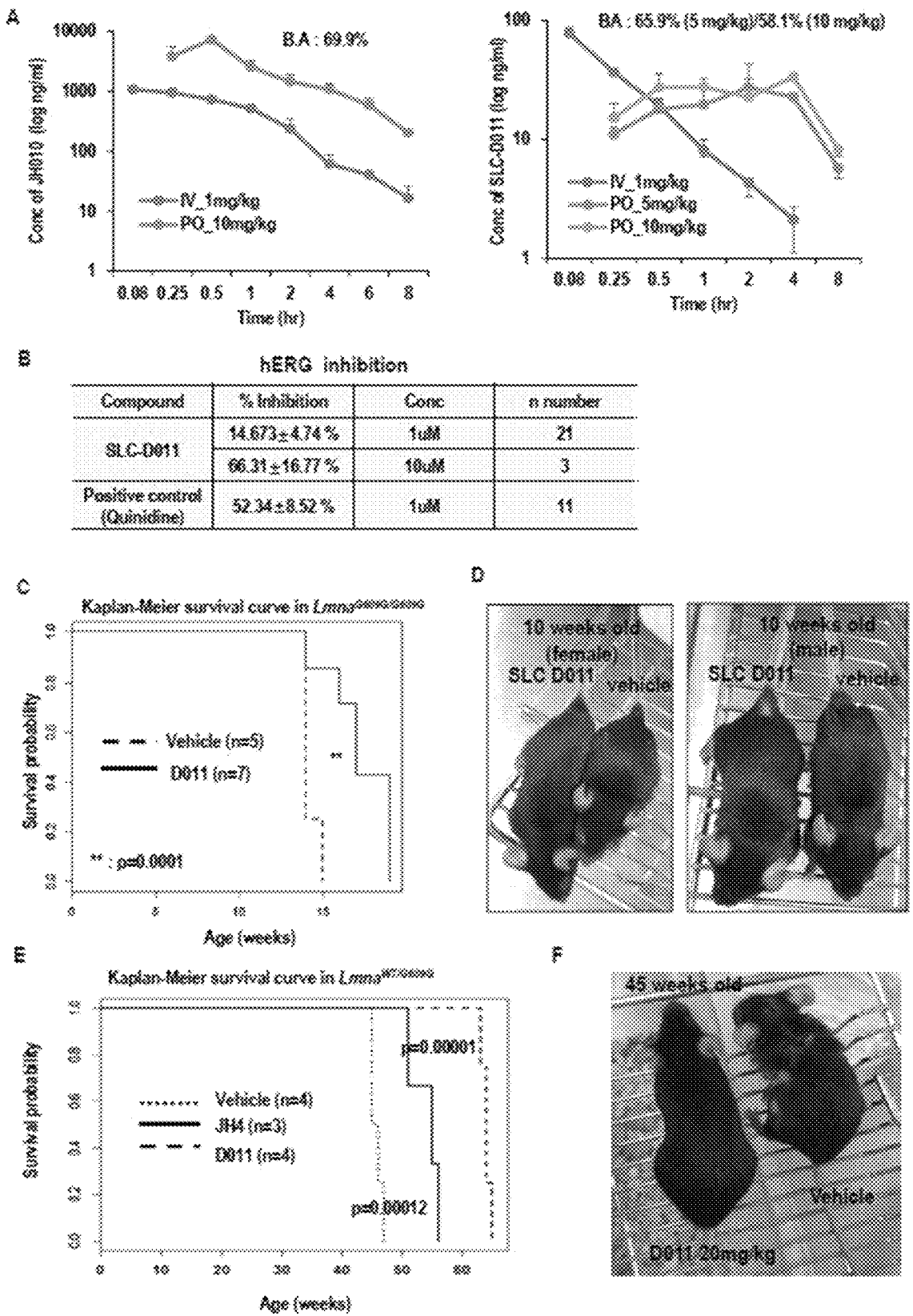

[FIG. 3]
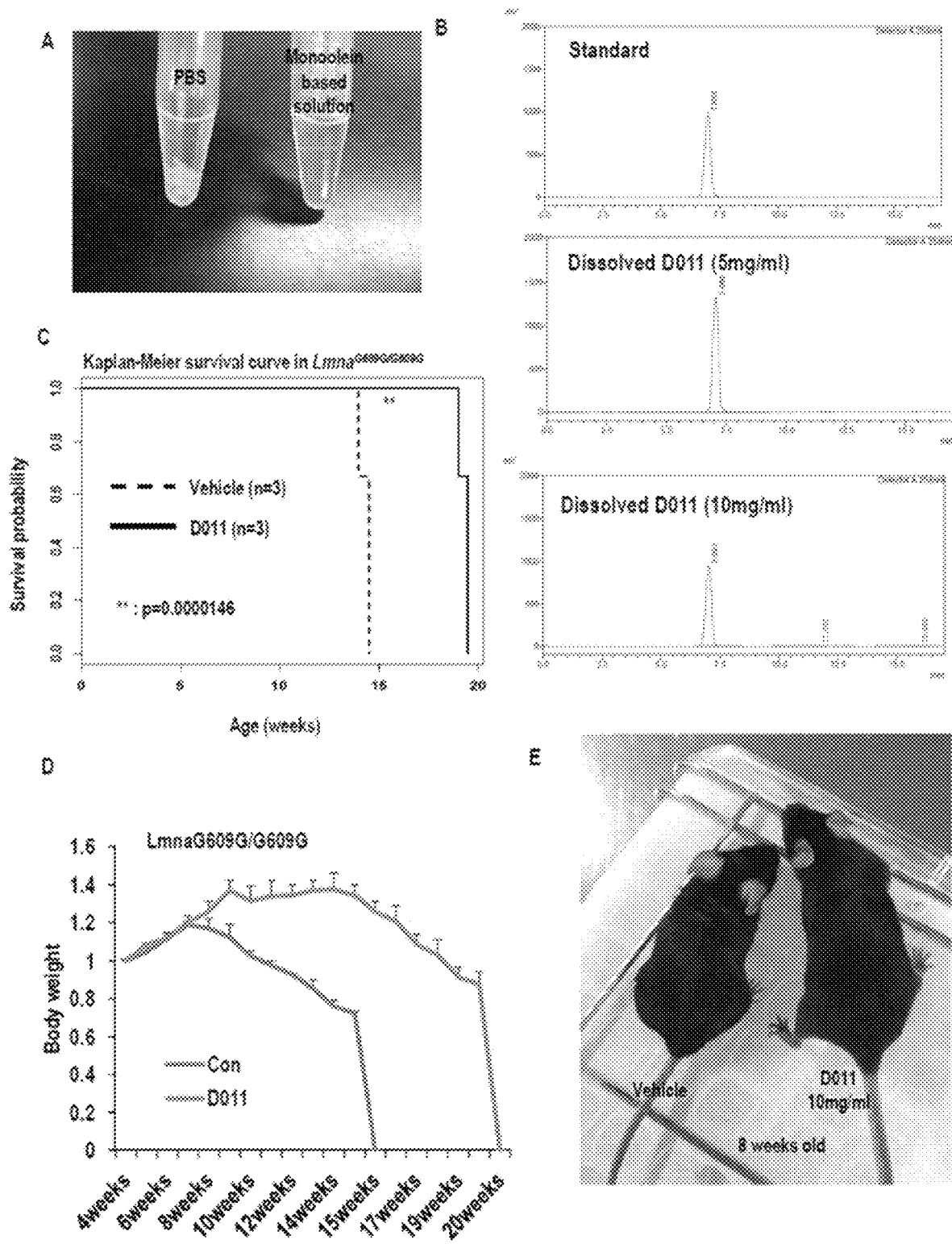

[FIG. 4]
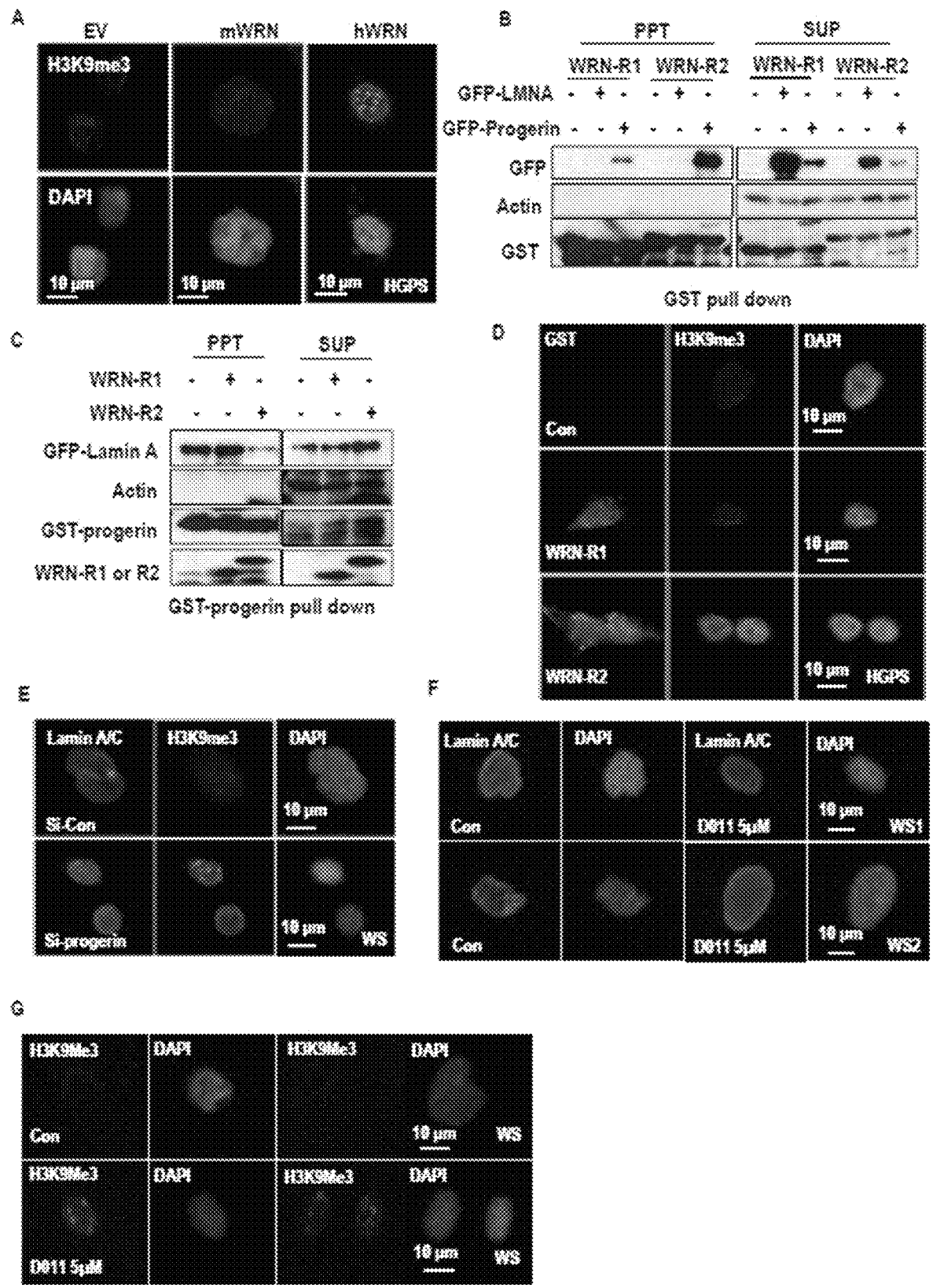

[FIG. 5]
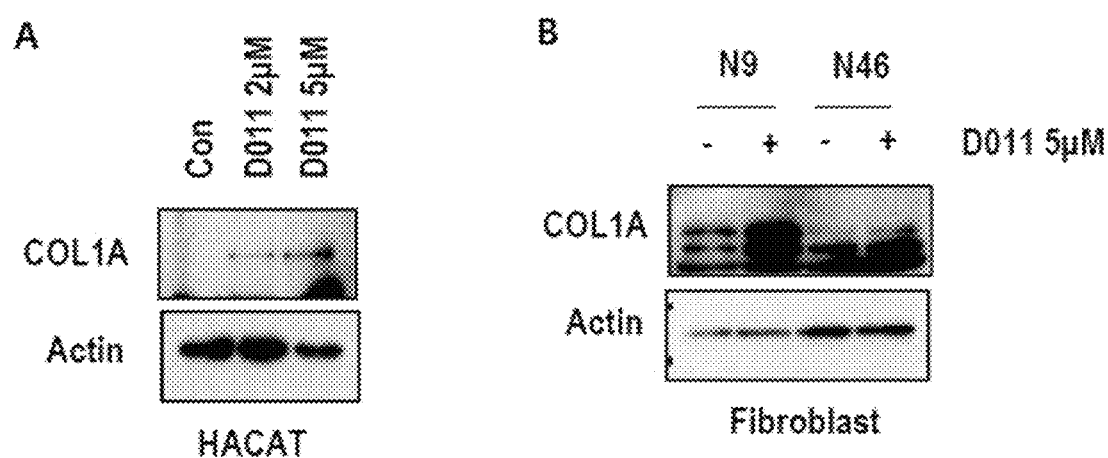

PHARMACEUTICAL COMPOSITION FOR PREVENTING OR TREATING AGING-RELATED DISEASES CONTAINING DECURSIN DERIVATIVE AS ACTIVE INGREDIENT

CROSS REFERENCE TO PRIOR APPLICATIONS

This application is a National Stage Application of PCT International Patent Application No. PCT/KR2018/004812 filed on Apr. 25, 2018, under 35 U.S.C. § 371, which claims priority to Korean Patent Application Nos. 10-2017-0052787 and 10-2018-0045593 filed on Apr. 25, 2017 and Apr. 19, 2018, respectively, which are all hereby incorporated by reference in their entirety.

TECHNICAL FIELD

The present invention relates to a novel decursin derivative and a composition for preventing or treating aging-related diseases comprising the same as an active ingredient.

BACKGROUND ART

As the lifespan of human increases, an interest in the aging progress has been actively raised, but there are still many areas that have not yet been clarified and recent studies have mainly focused on genetic or molecular aging mechanisms in human progeria.

Progeria or Hutchinson Gilford progeria syndrome (HGPS) is a fatal and rare genetic disorder that causes premature aging in young children. Children with progeria show normal appearance in early infancy, but serious growth retardation starts around about 9-24 months, resulting in a small height and a low weight. They have distinctive facial appearance, systemic atherosclerosis, cardiovascular disease, stroke, hip dislocation, loss of fat layer under the skin, defects of the nails, hardness of the joints, skeletal damage, etc. These pediatric patients with progeria usually die at the age of 8-21 due to heart diseases and their life expectancy is about 13 years old.

HGPS is a very rare autosomal dominant genetic disease caused by silent mutation of G608G of Lamin A (LMN A). The mutation produces a new truncated donor site and produces progerin (Prg), an alternative cleavage site product in which the 50 amino acids of the C-terminal domain of Lamin A have been deleted.

Expression of progerin leads to morphological changes such as nuclear membrane irregularity or decrease of nuclear-cytoplasmic Lamin A and inhibition of progerin expression induces the reduction of the nuclear deformation, which was confirmed as a major factor of HGPS.

Accordingly, the progeria can be treated by inhibiting farnesylation of the progerin or by removing the farnesylated Lamin A using autophage to relieve progerin, however In both cases there is a side effect problem and until now no fundamental treatment of the progeria has been reported.

DISCLOSURE

Technical Problem

The present invention provides a novel compound that inhibits the binding of progerin to Lamin A and provides a composition comprising the compound as an active ingredient as a pharmaceutical composition for preventing or treating aging-related diseases such as progeria.

Technical Solution

The present invention provides a compound represented by the following Chemical Formula 1 or a pharmaceutically acceptable salt thereof.

[Chemical Formula 1]

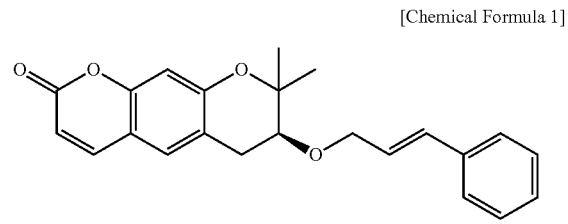 [SMILES: CC1(C)Oc2cc3oc(=O)ccc3cc2C[C@@H]1OC/C=C/c1ccccc1]

The present invention provides a pharmaceutical composition for preventing or treating an aging-related disease, comprising a compound represented by the following Chemical Formula 1 or a pharmaceutically acceptable salt thereof as an active ingredient.

[Chemical Formula 1]

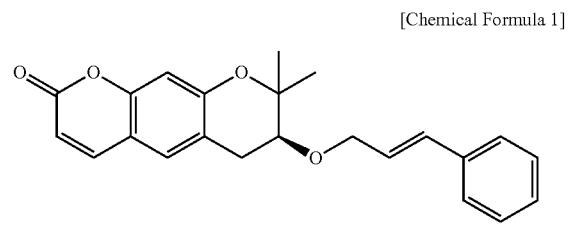 [SMILES: CC1(C)Oc2cc3oc(=O)ccc3cc2C[C@@H]1OC/C=C/c1ccccc1]

The present invention also provides a cosmetic composition for preventing or improving wrinkles comprising a compound represented by the following Chemical Formula 1 or a pharmaceutically acceptable salt thereof.

[Chemical Formula 1]

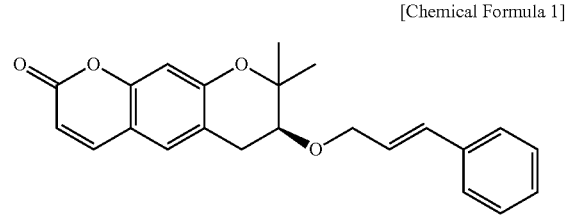 [SMILES: CC1(C)Oc2cc3oc(=O)ccc3cc2C[C@@H]1OC/C=C/c1ccccc1]

Advantageous Effects

The novel compounds according to the present invention showed excellent inhibition of progerin expression and progerin/Lamin A binding in progerin-induced cell and animal models, and in particular, as it has been confirmed that its oral administration inhibits the binding of progerin and Lamin A and prolongs the survival time of the animal model in which progeria is induced at similar levels of intraperitoneal injection, the compounds of the present invention can be effectively used for the treatment of aging-related diseases such as Hutchinson Gilford progeria syndrome (HGPS) and Werner syndrome, and the novel compound of the present invention can be provided as a cosmetic composition for preventing or improving wrinkles by confirming that it increases the collagen production of skin cells.

DESCRIPTION OF DRAWINGS

FIG. 1 shows optimization of progerin-Lamin A binding inhibitor. FIG. 1A shows the results of in vivo PK analysis of JH4 confirming that although JH4 can obviously suppress premature aging phenotypes in progeria model mouse via i.p injection, it was very rapidly disappeared by PO treatment. FIG. 1B shows generation of JH4 derivatives which is synthesized by replacing side chain with amide bond (JH010) or ether bond (SLC-D011) to prevent rapid digestion in in vivo. FIG. 1C shows the result confirming that JH4 derivatives inhibit Lamin A (LMNA) and progerin interaction and binding inhibition assay results after that bead-conjugated LMNA was incubated with GFP-progerin transfected 293 cell lysate with indicated chemicals. FIG. 1D shows the result confirming that SLC-D011 (D011) obviously suppresses progerin expression and for progerin expression analysis, each chemical was treated to progerin-transfected 293 cells for 24 hours comparing to JH4 or JH010, D011 obviously suppressed the progerin expression. FIG. 1E shows the results of confirming that D011 ameliorates nuclear morphology and reduces progerin expression and HGPS cells (AG03198, 10-year-old female; AG03199; 10-year-old female) were incubated with chemicals for 48 hr and stained with progerin (red) and abnormal morphology of nucleus was ameliorated by chemicals, in particular, D011. DAPI indicated DNA. FIG. 1F shows the result confirming that JH010 and D011 can induce H3K9me3 expression and since H3K9me3 reduction is one of well-known marker for premature aged cells, H3K9me3 expression was evaluated by immunostaining and both chemicals could induce H3K9me3 expression in HGPS cell.

FIG. 2 shows in vivo favorable effect of SLC-D011. FIG. 2A shows in vivo PK analysis of JH010 and SLC-D011. Both chemicals showed the proper PK profile and B.A indicates bioavailability. FIG. 2B shows the result confirming that since JH010 show human ERG (hERG) inhibition, the effect of SLC-D011 on hERG is determined and SLC-D011 did not show severe hERG inhibition. FIG. 2C shows the result confirming that SLC-D011 extends the life span of $Lmna^{G609G/G609G}$, progeria model mouse and comparing to 14.8 weeks of average (ave) life span (maximum (max) life span is 15 weeks), 20 mg/kg of i.p injection (twice per week) of SLC-D011 could extend the life span to 19.5 weeks (max=21 weeks). $Lmna^{G609G/G609G}$ Mice were injected from 5 week age old. FIG. 2D shows the result of gross morphology of injected $Lmna^{G609G/G609G}$ mice (10 weeks old). It was confirmed that at the same age, injected mice were larger than control mice. FIG. 2E shows the effect of SLC-D011 on life span of $Lmna^{wt/G609G}$ mice. It was confirmed that comparing to vehicle (ave=44.6 and max=46) and JH4 (ave=54 and max=56) injected groups, SLC-D011 treatment could obviously extend the average life span to 65 weeks (max=66). Injection was started from 43 weeks old. FIG. 2F shows the gross morphology of D011 injected $Lmna^{wt/G609G}$ mouse. Sickly and weak features of 45 weeks old $Lmna^{wt/G609G}$ mouse were not observed in treated mouse, despite the same age.

FIG. 3 shows the results confirming that oral administration of SLC-D011 can suppress premature aging features. FIG. 3A shows the formulation for complete dissolution. Due to extremely hydrophobic property of SLC-D011, it is not dissolved in water solution (left). To overcome this problem, several edible solutions in which All components are already used for medical formulation, were tested and, finally, monoolein based solution was selected for dissolving solution (right). FIG. 3B shows the result confirming that SLC-D011 is very stable. For completely dissolution, heating at 80° C. and sonication step were required. However, despite heating and sonication, SLC-D011 was not broken down and original chemical and completely dissolved chemical showed the same pattern in LC-MS. FIG. 3C shows the result confirming that oral administration of SLC-D011 can extend the life span of $Lmna^{G609G/G609G}$ mice. SLC-D011 in monoolein solution was treated by oral gavage (50 mg/kg, daily) from 5 weeks old. Comparing to vehicle (ave=14.9 and max=15.5), treated group showed extended life span (ave=19.3 and max=19.5). FIG. 3D shows the result confirming that oral administration of SLC-D011 can increase body weight in $Lmna^{G609G/G609G}$ mice. Comparing to vehicle group, body weight of treated mice was increased about 35%. FIG. 3E shows the result of gross morphology of SLC-D011 treated mice at 8 weeks old. Body size of treated mouse was apparently larger than that of vehicle-mouse.

FIG. 4 shows that SLC-D011 can ameliorate the premature aging features of Werner syndrome cells. FIG. 4A shows the result confirming that HGPS cells were transfected with indicated vectors for 48 hr and stained with H3K9me3 antibody after fixation and transfection of human WRN (hWRN), but not mouse WRN (mWRN), induces H3K9me3 expression in HGPS cells. FIG. 4B shows that human unique duplicated region is critical for progerin-WRN binding. Bead-conjugated GST WRN-R1 (non-repeated peptide) and WRN-R2 (duplicated peptide) were incubated with GFP-LmnA or progerin transfected 293 cell lysates. After pull down assay by centrifugation, bound GFP proteins were measured by Western Blotting analysis. FIG. 4C shows the result confirming that WRN-R2 blocks the interaction of Lamin A and progerin. Bead conjugated GST-progerin was incubated with GFP-Lamin A transfected 293 lysate with or without WRN-R1 or R2 and by addition of recombinant WRN-R2, Lamin A-progerin interaction was obviously reduced. FIG. 4D shows the result confirming that using the protein delivery agent, WRN-R1 and R2 peptides were inserted into HGPS cells for 24 hr and recombinant WRN-R2 peptide can induce H3K9me3 and ameliorate nuclear abnormality. In WRN-R2 delivered cells, increase of H3K9me3 expression and improvement of nuclear shape were observed. FIG. 4E shows that elimination of progerin can induce H3K9me3 in Werner syndrome (WS) patient cells. WS cells were transfected with si-control (non-target sequence) or si-progerin for 48 hr and stained with H3K9me3 antibody and DAPI (for nucleus) and progerin knock-down using siRNA showed the induction of H3K9me3 and reduction of nuclear size in WS cells. FIG. 4F shows the results confirming that SLC-D011 ameliorates nuclear abnormality of WS cells and WS cells were incubated with SLC-D011 for 48 hr and stained with Lamin A/C antibody and DAPI. FIG. 4G shows that WS cells were incubated with SLC-D011 for 48 hr and subjected into IF staining and SLC-D011 can induce H3K9me3 expression in WS cells. Extremely low expressed H3K9me3 in WS cells was apparently induced by SLC-D011 treatment.

FIG. 5 shows the results of confirming the effect of SLC-D011 on HaCaT cells which is human skin keratinocytes and fibroblasts. FIG. 5A shows Western blot analysis of collagen 1A expression in HaCaT cells after that HaCaT cells were treated with SLC-D011 and incubated for 24 hours. FIG. 5B shows the result of Western blot analysis confirming the amount of expression of collagen 1A after that SLC-D011 treated with normal fibroblast 9N (GM 00038, 9-year-old to female) and N46 (AG13299, 46-year-old male).

BEST MODE

The present invention can provide a compound represented by the following Chemical Formula 1 or a pharmaceutically acceptable salt thereof.

[Chemical Formula 1]

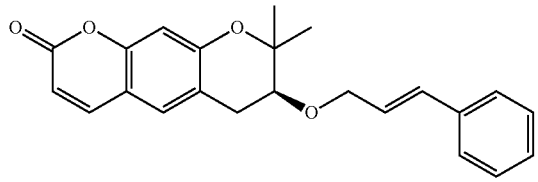

The present invention can provide a pharmaceutical composition for preventing or treating an aging-related disease, comprising a compound represented by the following Chemical Formula 1 or a pharmaceutically acceptable salt thereof as an active ingredient.

[Chemical Formula 1]

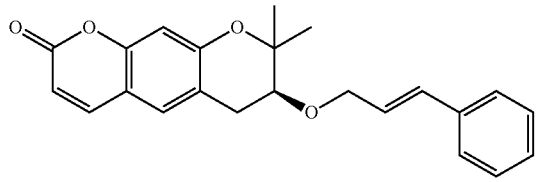

More particularly, the compound represented by Chemical Formula 1 or a pharmaceutically acceptable salt thereof may be (7S)-(+)-8,8-dimethyl-7-(3-phenyl-allyoxy)-7,8-dihydro-6H-pyrano[3,2-g]chromen-2-one (SLC-D011).

The aging-related disease may be progeria.

More specifically, the progeria may be selected from the group consisting of Werner syndrome and Hutchinson Gilford progeria syndrome.

The compound represented by Chemical Formula 1 and the pharmaceutically acceptable salt thereof can inhibit the binding between progerin and Lamin A.

In one embodiment of the present invention, the pharmaceutical composition may be used as any one formulation selected from the group consisting of injections, granules, powders, tablets, pills, capsules, suppositories, gels, suspensions, emulsions, drippers or liquids, in any conventional manner.

In another embodiment of the present invention, the pharmaceutical compositions may comprise at least one additive selected from the group consisting of carriers, excipients, disintegrants, sweeteners, coatings, swelling agents, slip modifiers, flavors, antioxidants, buffers, bacteristats, diluents, dispersants, surfactants, binders and lubricants.

Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

According to one embodiment of the present invention, the pharmaceutical composition may be administered intravenously, intraarterially, intraperitoneally, intramuscularly, intraperitoneally, intrasternally, transdermally, nasally, inhaled, topically, rectally, orally, intraocularlly or intradermally to the subject in a conventional manner.

The preferred dose of the compound represented by the Chemical Formula 1 may vary depending on the condition and body weight of the subject, the type and degree of the disease, the drug form, the administration route and the period, and may be appropriately selected by those skilled in the art. According to one embodiment of the present invention, the daily dose may be 0.01 to 200 mg/kg, specifically 0.1 to 200 mg/kg, more specifically 0.1 to 100 mg/kg, though it is not limited thereto. The administration may be performed once a day or in divided into several times, and thus the scope of the present invention is not limited thereto.

In the present invention, the 'subject' may be a mammal including a human, but it is not limited thereto.

The present invention also can provide a cosmetic composition for preventing or improving wrinkles comprising a compound represented by the following Chemical Formula 1 or a pharmaceutically acceptable salt thereof.

[Chemical Formula 1]

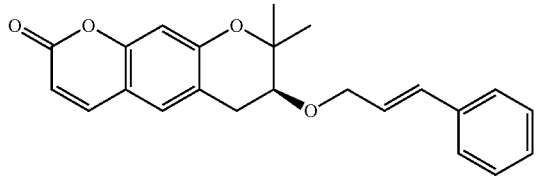

The compound represented by Chemical Formula 1 and the pharmaceutically acceptable salts thereof can improve collagen production in keratinocytes and fibroblasts.

The cosmetic composition may contain, in addition to the compound represented by the Chemical Formula 1 as an active ingredient, conventional additives such as stabilizers, solubilizers, vitamins, pigments and flavors, and carriers.

The cosmetic composition may be prepared in any formulation conventionally produced in the art such as solution, suspension, emulsion, paste, gel, cream, lotion, powder, oil, powder foundation, emulsion foundation, wax foundation, spray, and the like, but it is not limited thereto. More specifically, it can be prepared in the formulation of a sun cream, a skin lotion, a convergent lotion, a nutritional lotion, a nutritional cream, a massage cream, an essence, an eye cream, a pack, a spray or a powder.

When the formulation is a paste, cream or gel, an animal oil, a vegetable oil, a wax, a paraffin, a starch, a tragacanth, a cellulose derivative, polyethylene glycol, silicone, bentonite, silica, talc or zinc oxide may be used as a carrier component.

When the formulation is a powder or a spray, lactose, talc, silica, aluminum hydroxide, calcium silicate or polyamide powder may be used as a carrier component. Especially, the spray may further comprise chlorofluorohydrocarbons, propane/butane or propellants such as dimethyl ether.

When the formulation is a solution or an emulsion, a solvent, a solubilizing agent or an emulsifying agent is used as a carrier component, and examples thereof include water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid esters of sorbitan.

When the formulation is a suspension, a liquid diluent such as water, ethanol or propylene glycol, a suspension such as ethoxylated isostearyl alcohol, polyoxyethylene sorbitol ester and polyoxyethylene sorbitan ester, a microcrystalline cellulose, aluminum metahydroxide, bentonite, agar or tragacanth, etc. may be used as a carrier component.

Hereinafter, the present invention will be described in detail with reference to the following examples. However, the following examples are intended to illustrate the contents of the present invention, but the scope of the present invention is not limited to the following examples. The Examples of the present invention are provided to more fully describe the present invention to those skilled in the art.

<Reference Example> Materials and Equipment

The $^1$H and $^{13}$C NMR spectra were measured using a JNM-AL 400 spectrometer (400 MHz, JEOL, Japan) and the melting point was measured using an Electrothermal melting point apparatus (Yamaco. MD-S3) and the mass spectrometry was performed using an API 2000 LC/MS/MS spectrometer (PE Sciex, Canada).

The optical rotations were measured on a JASCO DIP-360 automatic digital polarimeter. The purity of the chiral material was determined by HPLC (Shimadzu LC-6AD, Japan), column (CHIRACEL OD-H 0.46 cmϕ×25 cm, DAICEL CHEMICAL IND., Co. Osaka, Japan).

SiliaFlash®P60 (SILICYCLE, 230~400 mesh) was used for silica gel to separate material and TLC silica gel 60 F254 (MERCK) were used for the thin film TLC plate.

The solvents and reagents used in the synthesis of the materials were purchased from Sigma-Aldrich, Fluka, TCI, Junsei, Duksan pure chemical, SK Chemical and SAMCHUN chemical as reagent grade.

<Example 1> Synthesis of Ether-Form (+)-Decursin Derivative (SLC-D011)

(7S)-(+)-8,8-dimethyl-7-(3-phenyl-allyloxy)-7,8-dihydro-6H-pyrano[3,2-g]chromen-2-one (SLC-D011) was synthesized through the manner as in the to following Reaction Schemes 1 and 2.

1. Synthesis Process I

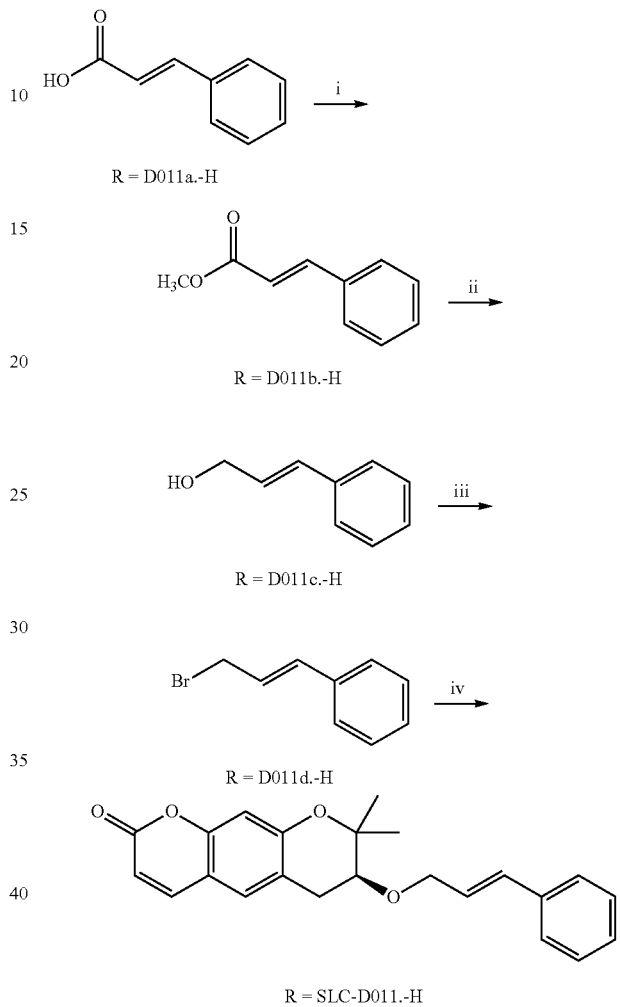

[Reaction Scheme 1]

Step (I): After dissolving trans-cinnamic acid (D0111a, 5 g, 33.7 mmol) in methanol (50 ml) in a 100 ml round bottom flask, 5 drops of concentrated $H_2SO_4$ was added and the mixture was refluxed by heating at 80° C. for 24 hours and was cooled to room temperature and then concentrated under reduced pressure.

Then, the mixture was separated with dichloromethane (300 ml) and distilled water (300 ml) to collect the organic layer and dehydrated with sodium sulfate and filtered.

After filtration, the filtrate was concentrated under reduced pressure to obtain 3-phenyl-acrylic acid, methyl ester (D011b, 5.39 g, yield=98.5%) as a pure product to apply to the next step.

Step (II): 3-phenyl-acrylic acid, methyl ester (D011b, 4 g, 24.7 mmol, 1 eq) was added into a 500 ml round bottom flask filled with $N_2$ gas and was dissolved in anhydrous dichloromethane and then placed in a low-temperature reactor set at −78° C.

Diisobutylaluminium hydride 1M solution (DIBAL-H; 1M solution in hexane, 74 ml, 74.0 mmol, 3 eq) was slowly added dropwise over 30 minutes to the reaction solution and methanol (22 ml) was slowly added dropwise while the reaction temperature was raised to 0° C. and stirring was carried out for 1 hour.

The reaction solution was transferred to room temperature, stirred for 30 minutes and then a saturated aqueous solution of Rochelle's salt (88 ml) was added thereto.

The reaction mixture was vigorously stirred at room temperature for 2 hours, and the mixture was partitioned twice with dichloromethane (300 ml) and distilled water (300 ml) to collect the organic layers and was dehydrated with sodium sulfate, filtered and the resulting filtrate was concentrated under reduced pressure.

The concentrate was purified by silica gel column chromatography (ethyl acetate:n-hexane=3:1) to obtain the pure product 3-phenyl-pro-2-pen-1-ol (D011c, 3.1 g, yield=93.9%, Rf=0.37 (2:1 n-hexane-ethyl acetate) to apply to the next step.

Step (III): To a 100 ml round bottom flask was added 3-phenyl-pro-2-pen-1-ol (D011c, 1 g, 7.45 mmol, 1 eq), was dissolved in anhydrous dichloromethane, PBr$_3$ (phosphoric tribromide, 253.6 µl, 2.608 mmol, 0.35 eq) was added on the steam bath and stirred for 1 hour.

The reaction mixture was concentrated and purified by silica gel column chromatography (ethyl acetate:n-hexane=1:8) to obtain the pure product, 3-bromo-propenyl)-benzene (D005d, 1.42 g, yield=96.2%, Rf=0.34 (5:1 n-hexane-ethyl acetate) which was applied to the next step.

Step (IV): (S)-(+)-decursinol (SLC-B001, 2.33 g, 9.47 mmol, 1 eq) was dissolved in anhydrous N,N-dimethylformamide (DMF, 10 ml) in a 100 ml round bottom flask under an N$_2$ gas and was placed in a low temperature reactor set at −20° C.

(3-bromo-propenyl)-benzene (D005d, 2.8 g, 14.2 mmol, 1.5 eq) and sodium sulfate (NaH 60%, 757 mg, 18.9 mmol) were added to the reaction mixture and stirred for 4 hours. 3 ml of distilled water was added and after 10 minutes, it was taken out from the low-temperature reactor. Then, it was separated into twice with dichloromethane (200 ml) and distilled water (200 ml) to collect the organic layer and dehydrated with sodium sulfate, filtered and the resulting filtrate was concentrated under reduced pressure.

The concentrate was separated by silica gel column chromatography (ethyl acetate:n-hexane=gradient elution to 1:3 from 1:10) to obtain (7S)-(+)-8,8-dimethyl-7-(3-phenyl-allyloxy)-7,8-dihydro-6H-pyrano[3,2-g]chromen-2-one (SLC-D011) of 1.21 g, (35.3%). Yield 35.3%, white solid, mp: 143° C., R$_f$=0.39 (2:1 n-hexane-ethyl acetate); $[\alpha]^{25}_D$+ 117.6 (c=1, CHCl$_3$); $^1$H NMR (400 MHz, CDCl$_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=6.0, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s CH$_3$-8), 1.36 (3H, s, CH$_3$_8); $^{13}$C NMR (100 MHz, acetone-d$_6$) $\delta_C$ 161.2 (C-2), 157.8 (C-9a), 155.3 (C-10a), 144.5 (C-4), 137.9 (C-4'), 132.9 (C-3'), 130.4 (C-5), 129.6 (C-6', C-8'), 128.6 (C-7'), 127.5 (C-2'), 127.4 (C-5', C-9'), 118.3 (C-5a), 113.7 (C-3), 113.6 (C-4a), 104.5 (C-10), 78.8 (C-7), 76.4 (C-8), 70.8 (C-1'), 27.8 (C-6), 26.1 (CH$_3$-8), 22.2 (CH$_3$-8); ESI-MS: m/z=363 [M+H]$^+$. Anal. Calc. for C$_{23}$H$_{22}$O$_4$: C, 76.22; H, 6.12; Found: C, 76.20; H, 6.10.

2. Synthesis Process II

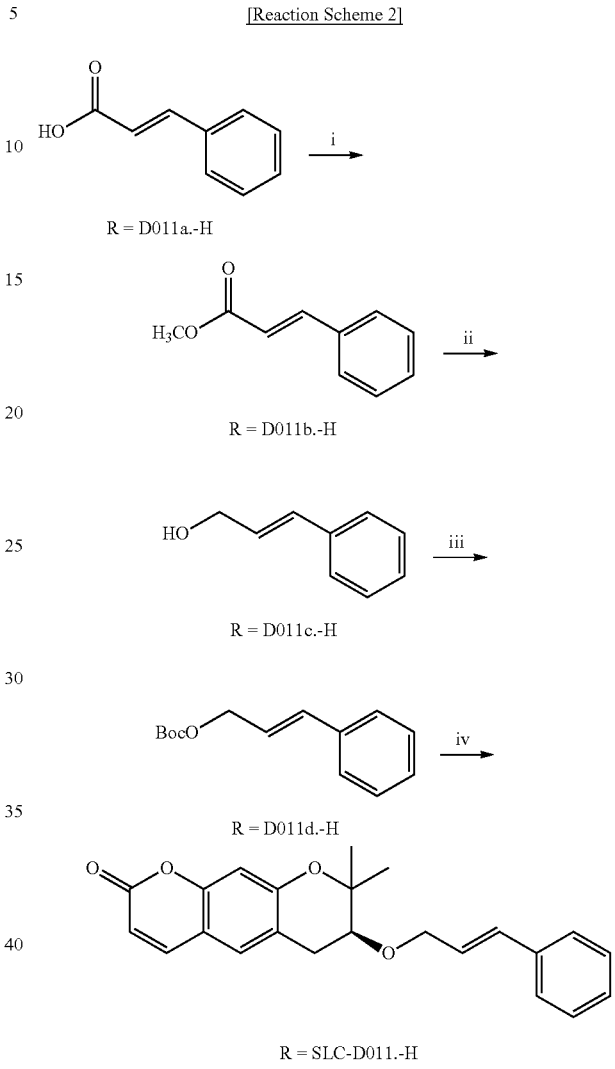

[Reaction Scheme 2]

Step (I): After dissolving trans-cinnamic acid (D011a, 5 g, 33.7 mmol) in methanol (50 ml) in a 100 ml round bottom flask, 5 drops of concentrated H$_2$SO$_4$ was added and the mixture was refluxed by heating at 80° C. for 24 hours. The reaction mixture was cooled to room temperature and then concentrated under reduced pressure and was separated with dichloromethane (300 ml) and distilled water (300 ml) to collect the organic layer and dehydrated with sodium sulfate and filtered.

After filtration, the obtained filtrate was concentrated under reduced pressure to obtain 3-phenyl-acrylic acid, methyl ester (D011b, 5.39 g, yield=98.5%) as a pure product which was applied to the next step.

Step (II): 3-phenyl-acrylic acid, methyl ester (D011b, 4 g, 24.7 mmol, 1 eq) was added into a 500 ml round bottom flask filled with N$_2$ gas and was dissolved in anhydrous dissolved in anhydrous dichloromethane and then placed in a low-temperature reactor set at −78° C.

Diisobutylaluminium hydride 1M solution (DIBAL-H; 1M solution in hexane, 74 ml, 74.0 mmol, 3 eq) was slowly added dropwise over 30 minutes to the reaction solution and methanol (22 ml) was slowly added dropwise while the reaction temperature was raised to 0° C. and stirring was carried out for 1 hour.

The reaction solution was transferred to room temperature, stirred for 30 minutes and then a saturated aqueous solution of Rochelle's salt (88 ml) was added thereto. The reaction mixture was vigorously stirred at room temperature for 2 hours, and the mixture was partitioned twice with dichloromethane (300 ml) and distilled water (300 ml).

The organic layers were collected and were dehydrated with sodium sulfate, filtered and the resulting filtrate was concentrated under reduced pressure.

The concentrate was separated by silica gel column chromatography (ethyl acetate:n-hexane=3:1) to obtain the pure product 3-phenyl-pro-2-pen-1-ol (D011c, 3.1 g, yield=93.9%, Rf=0.37 (2:1 n-hexane-ethyl acetate) which was applied to the next step.

Step (III): 3-phenyl-prop-2-pen-1-ol (D011c, 1 g, 7.45 mmol, 1 eq) was added to a 100 ml round bottom flask filled with $N_2$ gas and was dissolved in anhydrous dichloromethane, and trimethylamine ($Et_3N$, 1.04 ml, 7.45 mmol, 1 eq), 4-dimethylaminopyridine (4-DMAP, 92 mg, 0.75 mmol, 0.1 eq), di-tert-butyl-dicarbonate (0.13 ml, 7.45 mmol, 1 eq), 4-dimethylaminopyridine (4-DMAP, 92 mg, 0.75 mmol, tert-butyl-dicarbonate (Boc2O, 2.57 ml, 11.18 mmol, 1.5 eq) were sequentially added, and the reaction solution was stirred at room temperature for 2 hours.

The reaction mixture was concentrated and separated by silica gel column chromatography (ethyl acetate:n-hexane=1:30) to obtain the pure product, tert-butyl cinnamyl carbonate (D011d, 1.30 g, yield=74.7%, Rf=0.32 (20:1 n-hexane-ethyl acetate)) which was applied to the next step.

Step (IV): Tert-butyl cinnamyl carbonate (D011d, 1.43 g, 6.09 mmol, 1.5 eq), (S)-(+)-decursinol (SLC—4.06 mmol, 1 eq) were added into a 100 ml round bottom flask and the mixture was dried under vacuum for 1 hour.

The dried mixture was dissolved in anhydrous tetrahydrofuran under $N_2$ gas and after bubbling the solution for 1 hour using $N_2$ gas, tetrakis(triphenylphosphine) palladium (Pd $(PPh_3)_4$, 188 mg, 0.162 mmol, 0.04 eq) was added to the reaction mixture and was refluxed overnight. The mixture liquid was concentrated under reduced pressure, and was separated by silica gel column chromatography (ethyl acetate:n-hexane=gradient elution to 1:4 from 1:8) to obtain compound (7S)-(+)-8,8-dimethyl-7-(3-phenyl-allyloxy)-7, 8-dihydro-6H-pyrano[3,2-g]chromen-2-one (SLC-D011) of 1.20 g (81.3%). Yield 81.3%, white solid, mp: 143° C., $R_f$=0.39 (2:1 n-hexane-ethyl acetate); $[\alpha]^{25}_D$+117.6 (c=1, $CHCl_3$); $^1H$ NMR (400 MHz, $CDCl_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=6.0, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s $CH_3$-8), 1.36 (3H, s, $CH_3$-8); $^{13}C$ NMR (100 MHz, acetone-$d_6$) $\delta_C$ 161.2 (C-2), 157.8 (C-9a), 155.3 (C-10a), 144.5 (C-4), 137.9 (C-4'), 132.9 (C-3'), 130.4 (C-5), 129.6 (C-6', C-8'), 128.6 (C-7'), 127.5 (C-2'), 127.4 (C-5', C-9'), 118.3 (C-5a), 113.7 (C-3), 113.6 (C-4a), 104.5 (C-10), 78.8 (C-7), 76.4 (C-8), 70.8 (C-1'), 27.8 (C-6), 26.1 ($CH_3$-8), 22.2 ($CH_3$-8); ESI-MS: m/z=363 [M+H]+. Anal. Calc. for $C_{23}H_{22}O_4$: C, 76.22; H, 6.12; Found: C, 76.20; H, 6.10.

<Example 2> Confirmation of Effect of SLC-D011 as Lamin A (LMN A)-Progerin Binding Inhibitor 1. Animal Experiments The experiments were performed in the Association for Assessment and Accreditation of Laboratory Animal Care certified facility, in compliance with animal policies approved by Pusan National University.

$Lmna^{G609G/609G}$ mice were generated as timed mating of heterozygous $Lmna^{+/G609G}$ provided by Carlos López-Otín (Universidad de Oviedo, Asturias, Oviedo, Spain).

SLC-D011, mixed with DMOS and PBS, were intraperitoneally injected in mice (20 mg/kg twice per week from 5-week-old). In addition, SLC-D011 dissolved at a concentration of 10 mg/ml in monoolein-based solution was orally administered to mice in 5 times a week and control mice were treated in the same conditions by administering monoolein-based solution alone.

$Lmna^{G609G/609G}$ mice were treated with clear chemical solution throughout life span, starting from 5 weeks of age. $Lmna^{+/G609G}$ were treated via intraperitoneal, starting from 32 weeks of age.

2. Cell Culture and Reagents

Human fibroblast cells from HGPS patients (AG03198, 10-year-old female; AG03199; 10-year-old female), WS patients (AG06300, 37-year-old male; AG03141, 30-year-old female; AG00780, 60-year-old male) and controls (GM 00038, 9-year-old female) were obtained from the Coriell Cell Repositories (Camden, N.J., USA) and were maintained in EMEM, containing 15% FBS, 2 mM glutamine or HEMEM with 26 mM HEPES without antibiotics.

HEK293 cell line, obtained from ATCC, were maintained in liquid medium (DMEM) containing 10% FBS and 1% antibiotics at 37° C.

3. Antibodies and Reagents

Antibodies used for experiments included GFP (Full name; 1:1000; sc-9996; Santa Cruz Biotechnology); Glutathione S-transferase (GST; 1:5000; sc-138; Santa Cruz Biotechnology); Actin (1:10000; sc-47778; Santa Cruz Biotechnology); Lamin A/C (1:10000; sc-376248; Santa Cruz Biotechnology); Progerin (1:300; sc-81611; Santa Cruz Biotechnology); Progerin (1:300; ab66587; Abcam); H3K9me3 (1;2000; Ab8898; Abcam).

4. Recombinant Proteins

To produce the recombinant proteins, recombinant Lamin A C-terminal region (Lamin A-C) and Progerin C-terminal region (Progerin C), were produced by cloning of 100 AA from upstream of the termination codon through PCR.

WRN-R1 region (hWRN 424-450) and WRN-R2 region (hWRN 424-476) were generated by similar strategy. Each fragment was loaded on to GSH-agarose, and then eluted using a buffer containing 20 mM reduced glutathione after extensive washing.

The eluted fractions were further purified using an anion-exchange chromatography (HitrapQ) to obtain the following WRN-R1 and WRN-R2 amino acid sequences.

WRN-R1: HLSPNDNENDTSYVIESDEDELEMEMLK
WRN-R2: HLSPNDNENDTSYVIESDEDELEMEMLK HLSPNDNENDTSYVIESDEDELEMEMLK

5. Western-Blot Analysis

Whole-cell lysates were prepared in RIPA.

15 μg of cell extracts were separated by SDS-PAGE and transferred onto a PVDF membrane.

The membrane was incubated for 1 h to overnight at 4° C. with primary antibody, followed by reaction with a secondary antibody at room temperature for 1 h.

Peroxidase activity was detected by chemiluminescence with ECL kit (Intron, Seoul, Korea) as recommended by its manufacturer.

6. Protein-Protein Interaction Analyses

For the analysis of protein-protein interaction, Glutathione S-transferase (GST) pull-down assay was performed.

To detect the interaction, GST-bead-fused Lamin A-C-terminal region, Progerin-C-terminal region, WRN-R1 region or WRN-R2 region was incubated with GFP tagged Progerin (GFP-Progerin) and Lamin A (GFP-Lamin A) transfected HEK293 cell lysate for 30 min at RT.

After washing once with PBS, precipitated materials were collected and subjected into SDS-PAGE and western blot with anti-GFP and GST.

For the competition assay of WRN-R1 and R2 against progerin and Lamin A binding, bead-conjugated GST-progerin was incubated with GFP-Lamin A overexpressed 293 lysate with or without WRN-R1 or R2 recombinant protein.

7. Immunofluorescence Staining and Senescence-Specific Acidic 3-Galactosidase Activity Staining Cells were seeded on a cover glass and transfected with the indicated vectors.

After fixing with 100% methanol or 1% paraformaldehyde (PFA) for 1 h at 4° C., cells were incubated with blocking buffer (PBS+anti-human-Ab; 1:400) for 1 h.

After washing with PBS twice, cells were incubated with anti-Lamin A/C, Progerin or H3K9Me3 in blocking buffer (1:200) overnight and sequentially with anti-goat Ab-FITC or anti-rabbit Ab-rhodamin in blocking buffer (1:500) for 7 h and mounted, and nucleus was stained with DAPI. Thereafter Immunofluorescence signal was detected by fluorescence microscopy (Zeiss and Logos).

For senescence specific acidic-β-galactosidase activity staining, cells were washed once with PBS (pH 7.2), fixed with PBS containing 0.5% glutaraldehyde.

After washing with PBS, cells were stained in X-gal solution overnight at 37° C.

8. Plasmids Transfection and Protein Delivery

GFP-progerin and GFP-fused Lamin A expression vectors were provided by T. Misteli (National Cancer Institute [NCI], Bethesda, Md., USA) and the Myc-human WRN vector and Myc-mouse WRN vector were purchased from Addgene.

Transfection was performed using jetPEI (Polyplus Transfection) and PULSin (Polyplus Transfection, New York, USA) following the manufacturer's protocol.

To deliver WRN-R1 and R2 protein into HGPS cells, PULSin (Polyplus Transfection, New York, USA) was used as manufacturer protocol.

The recombinant protein (2 μg) was diluted with 200 μl of 20 mM Hepes. After dilution, PULSin reagent (8 μl) was added. The mixture is incubated for 15 min at room temperature (RT). After incubation, the mixture was added to the cell. After 3 hr, the serum-free medium was replaced to 10% FBS contained medium. After 4 hr incubation, mixture containing media was removed from wells and filled with fresh serum-containing media.

9. Cell Counting

For counting nuclear deformed cell, obtained immunofluorescence images were used. Nuclear membrane showing abnormalities, dependent on Lamin A staining, were counted from randomly selected field. Counted cells were calculated percentage.

To measure the cell proliferation, DAPI stained cells were counted from immunofluorescence images.

10. Chemical Pharmacokinetic (PK) Analysis and In Vitro ADME Test.

For PK analysis, 5 mg/kg of JH4 in 10% DMSO, 5% Tween 90 and 95% saline solution was intravenously injected and 10 mg/kg of JH4 in 10% NMP and 90% PEG400 solution was per orally delivered. At the setting time-points, blood concentration of JH4 was determined by LC-MS/MS analysis and the PK analysis for other chemicals was also tested by the similar protocol.

In vitro ADME studies (plasma protein binding, CYP inhibition, microsomal stability, plasma stability and hERG inhibition) were performed by New drug development center though standard protocols.

11. Confirmation of Effect of SLC-D011 as Progerin-Lamin A Binding Inhibitor

Hutchison-Gilford syndrome is a well-known progerin syndrome and a rare genetic disorder. Genetic causes include a single point mutation in Lamin A that results in abnormal donor junctions, thereby producing progerin which a C-terminal 50 amino acid was deleted internally from.

In the previous report, the inventors of the present invention have confirmed that the nuclear abnormality of HGPS cells is due to a very strong binding between Lamin A and progerin, and the progerin inhibitor (JH4) from Lamin A binding improved the nuclear deformation of HGPS cells and restored aging-related markers such as p16/INK4A, DNA-PK and H3K9me3 expression. In addition, JH4 treatment via intraperitoneal injection (i.p.) prolonged the progerin model mouse lifespan for about 4 weeks.

However, considering the patient's condition, HGPS patients have very thin blood vessel walls and therefore intravenous injection is not a suitable delivery method and therefore, the possibility for oral administration of JH4 was confirmed.

As a result, as shown in FIG. 1A, Tables 1 and 2, intravenously injected and orally administered JH4 showed a very short half-life in vivo, and thus the bioavailability (B.A.) could not be confirmed.

TABLE 1

Plasma concentration after intravenous injection at a dose of 5 mg/kg (n = 3)

| Time (hr) | Subject 1 | Subject 2 | Subject 3 | Mean (ng/ml) | SD |
|---|---|---|---|---|---|
| 0.08 | 3.3 | 4.6 | 6.3 | 4.7 | 1.5 |
| 0.25 | 1.7 | 1.1 | 1.8 | 1.5 | 0.4 |
| 0.5 | 0.5 | 0.7 | 0.5 | 0.6 | 0.1 |
| 1 | BQL | BQL | BQL | BQL | BQL |
| 2 | BQL | BQL | BQL | BQL | BQL |
| 4 | BQL | BOL | BQL | BQL | BQL |
| 8 | BQL | BQL | BQL | BQL | BQL |
| 24 | BQL | BQL | BQL | BQL | BQL |

BQL: Below Quantifiable Limit (<1 ng/ml)

TABLE 2

Plasma concentration after oral administration at a dose of 10 mg/kg (n = 3)

| Time (hr) | Subject 1 | Subject 2 | Subject 3 | Mean (ng/ml) | SD |
|---|---|---|---|---|---|
| 0.08 | BQL | BQL | BQL | BQL | BQL |
| 0.25 | BQL | BQL | BQL | BQL | BQL |
| 0.5 | BQL | BQL | BQL | BQL | BQL |
| 1 | BQL | BQL | BQL | BQL | BQL |
| 2 | BQL | BQL | BQL | BQL | BQL |
| 4 | BQL | BQL | BQL | BQL | BQL |
| 8 | BQL | BQL | BQL | BQL | BQL |
| 24 | BQL | BQL | BQL | BQL | BQL |

BQL: Below Quantifiable Limit (<1 ng/ml)

Accordingly, in order to obtain a stable compound in vivo, various compounds were modified from JH4 and GST-pull down assay and progerin expression analysis were performed to confirm other 41 kinds of JH4 derivatives. As a result, 1C, JH010 and SLC-D011 showed similar activity to JH4, and it was confirmed that they exhibited the effect of inhibiting progerin expression as shown in FIG. 1D.

Also, referring to FIG. 1E and FIG. 1F, JH010 and SLC-D011 compounds induced H3K9me3 expression and improved nuclear abnormality of HGPS cells.

PK analysis also showed that JH010 and SLC-D011 (progerinin) improved the bioavailability (B.A.) by 70% and 66%, respectively, as shown in FIG. 2A.

However, hERG ion channel inhibition of the JH010 compound was confirmed in in vitro ADME analysis, and as a result of confirming the effect of SLC-D011 on the hERG ion channel, severe hERG inhibition was not observed in SLC-D011 as compared with JH010 as shown in FIG. 2B, and SLC-D011 compounds were found to exhibit good plasma stability and a suitable range of CYP inhibition as shown in Tables 3 to 6.

TABLE 3

Plasma protein binding

| Compound | Human (% Bound) | Rat (% Bound) |
|---|---|---|
| SLC-D011 | 99.9 | 99.8 |
| Dexamethasone (Reference) | 62.1 | 78.8 |
| Warfarin (Reference) | 98.9 | 98.2 |

TABLE 4

Plasma stability (% remaining)

| | Human | | Rat | |
|---|---|---|---|---|
| Compound | 30 min | 120 min | 30 min | 120 min |
| SLC-D011 | >100 | >100 | 83.6 | 75.1 |

TABLE 5

Liver microsomal stability (% remaining during 30 min)

| Compound | Human (%) | Rat (%) | Mouse (%) |
|---|---|---|---|
| SLC-D011 | 21.5 | 17.4 | 59.7 |
| Verapamil (Reference) | 16.2 | | |

TABLE 6

CYP inhibition

| | CYP1A2 | CYP2C9 | CYP2C19 | CYP2D6 | CYP3A4 |
|---|---|---|---|---|---|
| SLC-D011 | 81.6 | 78.4 | 28.8 | 91.7 | 92.5 |
| Ketoconazole (Reference) | 97.3 | 95.4 | >100 | 98.4 | 29.9 |

To confirm the in vivo effect of SLC-D011 having stability confirmed as described above, i.p injection was performed. As a result, the life-span of $Lamn^{G609G/G609G}$ mice was extended to 20 weeks as shown in FIG. 2C and as shown in FIG. 2D, body size increase and gross morphology were also improved by SLC-D011 treatment.

That the lifespan of the mice from 45 to 64 weeks by treatment with SLC-D011 in the $Lamn^{wt/G609G}$ model is extended is especially interesting and referring to FIG. 2E, the result is remarkably improved as compared with JH4 which has prolonged the life to about 10 weeks. In addition, as shown in FIG. 2F, it was confirmed that the morphology of the mouse treated with SLC-D011 such as hair condition and body size was greatly improved.

From the above results, SLC-D011 can be proposed as a very excellent candidate for HGPS.

12. Confirmation of Effect of Oral Administration of SLC-D011

In addition to JH4, SLC-D011 exhibited very low water solubility and the screening for a suitable solution was performed to increase the dissolution rate of SLC-D011 because this low water solubility causes a problem for compound delivery via oral administration.

As a result, it was confirmed that a monoolein-based solution was useful for dissolving SLC-D011 as shown in FIG. 3A, and that SLC-D011 in solution was stable without being decomposed even by heating and ultrasonic treatment as shown in FIG. 3B.

In addition, an olein-based solution is well suitable for SLC-D011 carriers since it can increase intestinal absorption without toxicity.

SLC-D011 prepared in the form of oral administration by dissolving in an olein-based solution was orally administered to $Lamn^{G609G/G609G}$ mice and as a result of in vivo effect, it was confirmed that the lifespan of $Lamn^{G609G/G609G}$ mice was extended to 4.5 weeks and their body weight was increased.

From the above results, it was confirmed that olein-based SLC-D011 solution was very useful for HGPS treatment.

<Example 3> Confirmation of Effect of SLC-D011 as Therapeutic Agent for Werner Syndrome Because the progerin expression is increased due to aging, the effect of SLC-D011 was also confirmed in Werner syndrome (WS) and the normal aging model.

First, the relationship between the lack of the Werner gene (WRN) and the progerin was confirmed. According to the previous report, the weight and lifespan of the mice in which the WRN expression was inhibited were not clearly different from those of the wild-type mice. Also in the present invention, it was confirmed that the lifespan and body weight of the mWRN$^{-/-}$ mice did not show any difference from those of the $Lamn^{wt/G609G}$ mice.

In addition, the amino acid sequences of mouse and human WRN were compared with each other and as a result, a specifically repeated sequence (WRN-R2) was identified in human WRN was confirmed. In fact, overlapping hWRN occurred due to repeated cDNA.

To investigate the relationship between hWRN and progerin, human and mouse WRNs were transfected into HGPS cells and nuclear morphology and H3K9me3 expression were confirmed.

As a result, interestingly, nuclear deformation was improved only in hWRN as shown in FIG. 4A and H3K9me3 expression was induced. In addition, recombinant peptides were prepared from single and double-repeated amino acids and their interaction with progerin was confirmed.

As a result of comparing with WRN-R1, it was confirmed that the double peptide strongly binds to progerin as shown in FIG. 4B and it was confirmed that WRN-R2 blocks the interaction of progerin and Lamin A as shown in FIG. 4C.

As a result of the above results, it was confirmed that WRN-R2 is a natural progerin inhibitor and when recombinant WRN-R2 was treated to HGPS cells and WS cells, it was confirmed that as shown in FIG. 4D, as for the cells in which the recombinant WRN-R2 was delivered into HGPS cells, the nuclear morphology was normalized and H3K9me3 expression was improved.

However, it was confirmed that the WS cells in which progerin was deleted exhibit the above-mentioned effects and in order to confirm whether SLC-D011 can be used as a therapeutic agent for treating WS cells, WS cells are treated with SLC-D011 and nuclear morphology and cell proliferation were analyzed.

As a result, as shown in FIG. 4F, SLC-D011 improved nuclear morphology and cell proliferation similar to HGPS in WS patient cells, and induced expression of H3K9me3 as shown in FIG. 4G.

From the above results, it was confirmed that SLC-D011 can also be used for the treatment of Werner syndrome which is an adult progeria.

<Example 4> Confirmation of Improvement of Skin Aging Effect of SLC-D011 Compound In the previous experiment, it was confirmed that SLC-D011 compound has a therapeutic effect on aging-related diseases, thus confirming the effect of the compound on human skin keratinocyte HaCaT cells and fibroblasts.

Human keratinocyte HaCaT cells and normal fibroblast 9N (GM 00038, 9-year-old female) and N46 (AG13299, 46-year-old male) were treated with 2 or 5 μM SLC-D011 and incubated for 24 hours and then the amount of collagen 1A expression was confirmed in HaCaT cells and fibroblasts was confirmed.

As a result, as shown in FIG. 5A and FIG. 5B, it was confirmed that SLC-D011 showed an effect of increasing collagen expression in human fibroblasts and keratinocytes.

From the above results, it was confirmed that the SLC-D011 compound is suitable as a progerin-Lamin A binding inhibitor, and the SLC-D011 compound can be provided for oral administration and can be used as an effective therapeutic agent for treating progeria or composition for improving wrinkle.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of treating a progeria in a subject in need thereof, comprising: providing a pharmaceutical composition comprising a compound represented by a following Chemical Formula 1 or Chemical Formula 2 or a pharmaceutically acceptable salt thereof:

[Chemical Formula 1]

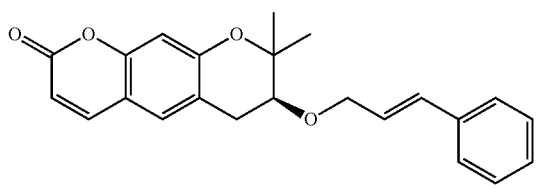

[Chemical Formula 2]

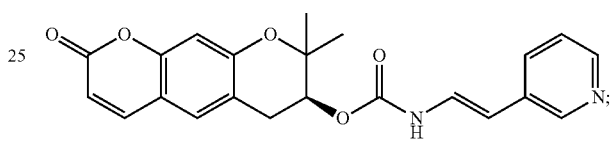

and
administering the pharmaceutical composition to the subject, wherein the progeria is treated.

2. The method of claim 1, wherein the compound represented by Chemical Formula 1 or pharmaceutically acceptable salt thereof is (7S)-(+)-8,8-dimethyl-7-(3-phenyl-allyloxy)-7,8-dihydro-6H-pyrano[3,2-g]chromen-2-one (SLC-D011) and the compound represented by Chemical Formula 2 or pharmaceutically acceptable salt thereof is (7S)-(+)-(E)-2-(pyridine-3-yl)ethenyl carbamic acid, 8,8-dimethyl-2-oxo-6,7-dihydro-2H,8H-pyrano[3,2-g]chromen-7-yl-ester (JH010).

3. The method of claim 1, wherein the progeria is selected from the group consisting of werner syndrome and Hutchinson Gilford progeria syndrome.

4. The method of claim 1, wherein the compound represented by Chemical Formula 1 or Chemical Formula 2 and the pharmaceutically acceptable salt thereof inhibit the binding between progerin and lamin A.

* * * * *